United States Patent [19]

Khanna et al.

[11] Patent Number: 5,130,481
[45] Date of Patent: Jul. 14, 1992

[54] BIS-N,N' NITRO OR AMINO BENZOYL AMINO PHENOLS

[75] Inventors: Dinesh N. Khanna, West Warwick; William R. Lee, East Providence, both of R.I.

[73] Assignee: Hoechst Celanese Corporation, Somerville, N.J.

[21] Appl. No.: 645,332

[22] Filed: Jan. 4, 1991

Related U.S. Application Data

[63] Continuation of Ser. No. 321,140, Mar. 9, 1989, abandoned.

[51] Int. Cl.$^5$ ............................................. C07C 237/00
[52] U.S. Cl. .................................... 564/157; 564/154; 564/155; 564/158
[58] Field of Search ................ 564/154, 155, 157, 158

[56] References Cited

U.S. PATENT DOCUMENTS 4,111,906  9/1978  Jones et al. .......................... 564/315

FOREIGN PATENT DOCUMENTS 6270424  3/1987  Japan .
2188936  10/1987  United Kingdom .

Primary Examiner—Richard L. Raymond
Assistant Examiner—Scott C. Rand
Attorney, Agent, or Firm—J. M. Hunter, Jr.

[57] ABSTRACT

Nitro dinitro and diamino compounds having the formula:

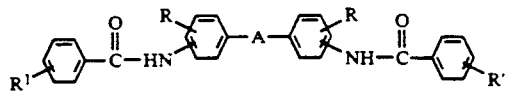

wherein A is selected from the group consisting of $SO_2$; O, S, CO, $C_1$ to $C_6$ alkylene, perfluoroalkylene or perfluoroarylalkylene having from 1 to 10 carbon atoms, and a carbon-carbon bond directly linking the two aromatic groups, R is selected from the group consisting of hydrogen, hydroxy and $C_1$ to $C_4$ alkoxy, and R' is selected from the group consisting of $NO_2$ and $NH_2$.

In the most preferred embodiment, the A linking group is selected from hexafluoroisopropylidene or 1-phenyl-2,- 2,2-trifluoroethane, and R is hydroxy.

The compounds of the present invention, where R' is $NH_2$, may be used as crosslinking agents for epoxy resins and for unsaturated elastomers, or as a reactant monomer with an organic diacid or dianhydride co-reactant monomer in the preparation of polyamide, polyimide, polyamide-imide and polybenzoxazole polymers having superior thermal and mechanical properties.

11 Claims, No Drawings

BIS-N,N' NITRO OR AMINO BENZOYL AMINO PHENOLS

This is a continuation of co-pending application Ser. No. 07/321,140 filed on Mar. 9, 1989, now abandoned.

BACKGROUND OF THE INVENTION

The present invention relates to novel bis-N,N'-amino benzoyl amines and aminophenols and bis-N,N'-nitro benzoyl amine and aminophenyl intermediate compounds. The amino compounds are useful as crosslinking agents and for the preparation of thermally stable polyamides, polyimides, polyamide-imides, and polybenzoxazole polymers.

Aromatic diamines having the structure $NH_2$—R—$NH_2$, where R is a substituted or unsubstituted aromatic moiety have long been known in the art as crosslinking agents for epoxy resins and for unsaturated elastomers, and as reactants in the preparation of polyamides, polyimides and polybenzoxazoles. For example, U.S. Pat. No. 4,111,906 discloses 2,2-bis[4-(4-nitrophenoxy)phenyl]hexafluoropropane which is used as an intermediate in the production of the corresponding amine, 2,2-bis[4-(4-aminophenoxy)phenyl]hexafluoropropane. This latter monomer is used in reaction with a dianhydride or a diacid to produce a polyimide or polyamide resin respectively. UK Patent Application GB2188936 A discloses the use of diaminophenols such as 2,2-bis(3-amino-4-hydroxyphenyl)hexafluoropropane to prepare aromatic polyamides by reaction with aromatic dicarboxylic acids, followed by cyclization of the polyamide to form a polybenzoxazole. Similar polyamides and polybenzoxazoles are also disclosed in U.S. Pat. No. 4,339,521.

European Patent Specification 0110420 discloses bis-(aminophenols) used as curing agents for nitrile-containing perfluoroelastomers. A preferred aminophenol is 4,4'[2,2,2-trifluoro-1-(trifluoromehtyl)-ethylidene]-bis(2-aminophenol), which is prepared by nitrating the corresponding bisphenol, followed by catalytic hydrogenation to reduce the dinitro intermediate to the diamine.

While the aforementioned diamines and aminophenols are useful in the applications taught in the prior art, there is a continuing need for new aminophenyl or aminocarboxy phenyl monomers which give rise to unusual and improved crosslinking properties as well as new polyamide, polyimide, and polybenzoxazole polymers exhibiting improved thermal properties, thermal flow properties and flexibility.

SUMMARY OF THE INVENTION

The present invention provides novel dinitro and diamino compounds having the formula:

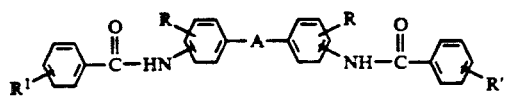

wherein A is selected from the group consisting of $SO_2$, O, S, CO, $C_1$ to $C_6$ alkylene, perfluoroalkylene or perfluoroarylalkylene having from 1 to 10 carbon atoms, and a carbon-carbon bond directly linking the two aromatic groups, R is selected from the group consisting of hydrogen, hydroxy and $C_1$ to $C_4$ alkoxy, and R' is selected from the group consisting of $NO_2$ and $NH_2$.

In the preferred embodiment, the R substituent and the amido substituent are interchangeably in the meta or para positions with respect to the A group, and R' is meta or para with respect to the amido linkage. In the most preferred embodiment, the A linking group is selected from hexafluoroisopropylidene or 1-phenyl-2,2,2-trifluoroethane, and R is hydroxy.

The compounds of the present invention, where R' is $NH_2$, may be used as crosslinking agents for epoxy resins and for unsaturated elastomers, or as a reactant monomer with an organic diacid or dianhydride co-reactant monomer in the preparation of polyamide, polyimide, polyamide-imide and polybenzoxazole polymers having superior thermal and mechanical properties.

DETAILED DESCRIPTION OF THE INVENTION

The compounds in accordance with formula I above may be prepared by a condensation reaction of a nitrobenzoyl halide having the formula:

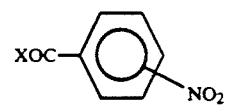

wherein X is halogen, preferably chlorine, and wherein the $NO_2$ group is para or meta with respect to the COX substituent group, with a compound having the formula:

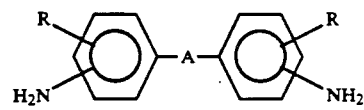

wherein A is selected from the group consisting of $SO_2$, O, S, CO, $C_1$ to $C_6$ alkylene, perfluoroalkylene or perfluoroarylalkylene having 1 to 10 carbon atoms or a carbon-carbon bond directly linking the two aromatic groups, and R is selected from the group consisting of hydrogen, hydroxy or $C_1$ to $C_4$ alkoxy.

In the more preferred embodiment of the present invention, A is a hexafluoroisopropylidene group ($CF_3$—C—$CF_3$) or a 1-phenyl-2,2,2 trifluoroethane group ($CF_3$—C—phenyl), and R is hydroxy. In the above formula, the $NH_2$ and R substituents are preferably interchangeably in the meta or para positions with respect to the A group.

Illustrative hydroxy-substituted or alkoxy-substituted aromatic diamines of formula III which may be employed in the practice of the present invention are: 3,3'-dihydroxy benzidine; 3,4'-diamino-3'4-dihydroxybiphenyl; 3,3'-dihydroxy-4,4'-diamino diphenyloxide; 3,3'-dihydroxy-4,4'-diamino diphenyl-sulfone; 2,2-bis-(3-amino-4-hydroxyphenyl)propane; bis(3-hydroxy-4-aminophenyl)methane; 3,3'-dihydroxy-4,4'-diamino benzophenone; 1,1-bis(3-hydroxy-4-aminophenyl)-ethane; 1,3-bis(3-hydroxy-4-aminophenyl)propane; 2,2-bis-(3-hydroxy-4-aminophenyl)propane, 1,1-bis(4-amino-3-hydroxyphenyl)-1-phenyl-2,2,2-trifluoroethane; 1,1-bis(4-hydroxy-3-amino-phenyl)-1-phenyl-2,2,2-trifluoroethane; 2,2-bis(4 amino-3-hydroxyphenyl)hexafluoropropane; 2,2-bis(3 amino-4-hydroxyphenyl)hexafluoropropane; and the analogous compounds where a $C_1$–$C_4$ alkoxy substituent replaces the hydroxy substituents, e.g., 3,3'-dimethoxy benzidene and the like. Also included are analogues of the above diamines containing no hydroxy or alkoxy substituent, such as benzidene and the like.

The preferred diamine for the purposes of this invention is 2,2-bis(3-amino-4-hydroxyphenyl)hexafluoropropane having the formula:

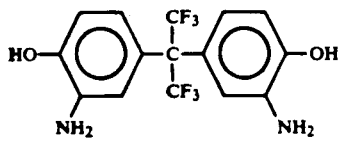

IV

The method of preparation of these compounds is known; see e.g., J. Polymer Sci., Vol. 20, p. 2381–2391 (1982).

Illustrative of preferred compounds of the formula II which may be condensed with formula III compounds are para-nitrobenzoyl chloride, para-nitrobenzoyl bromide, meta-nitrobenzoyl chloride and meta-nitrobenzoyl bromide.

The reaction sequence employed in the synthesis of the compounds of the present invention may be illustrated as follows:

amino substituent to form the amide linkage. The molar ratio of the amine and the benzoyl halide reacted is 1 to 2 respectively, although it is preferred to add the benzoyl halide in the reaction mixture at a molar excess of up to about 50%. Typically, the amine is first dissolved in a suitable solvent such as acetone, methyl ethyl ketone, dimethylacetamide or the like, and the benzoyl halide is then gradually added to this solution. The reaction may be best conducted with the assistance of an acid acceptor such as potassium carbonate, triethylamine, pyridine, and like condensation catalysts. The time required to effect the condensation in suitable yields will vary depending on the nature of the reactants and the reaction temperature. After the condensation reaction is complete, the desired product having the structure of formula (c) above is recovered from the reaction mixture and purified by conventional methods such as distillation, extraction or crystallization.

The resulting purified dinitro compound of formula (c) above is then reduced by treatment with a specific metal catalyst to form the corresponding diamines of formula (d). Suitable catalysts include finely divided metals such as platinum, palladium or ruthenium. The preferred catalyst is finely divided carbon having active palladium precipitated on the surface of the carbon. Reduction is most readily accomplished by forming a solution of the dinitro compound of formula (c) in suit-

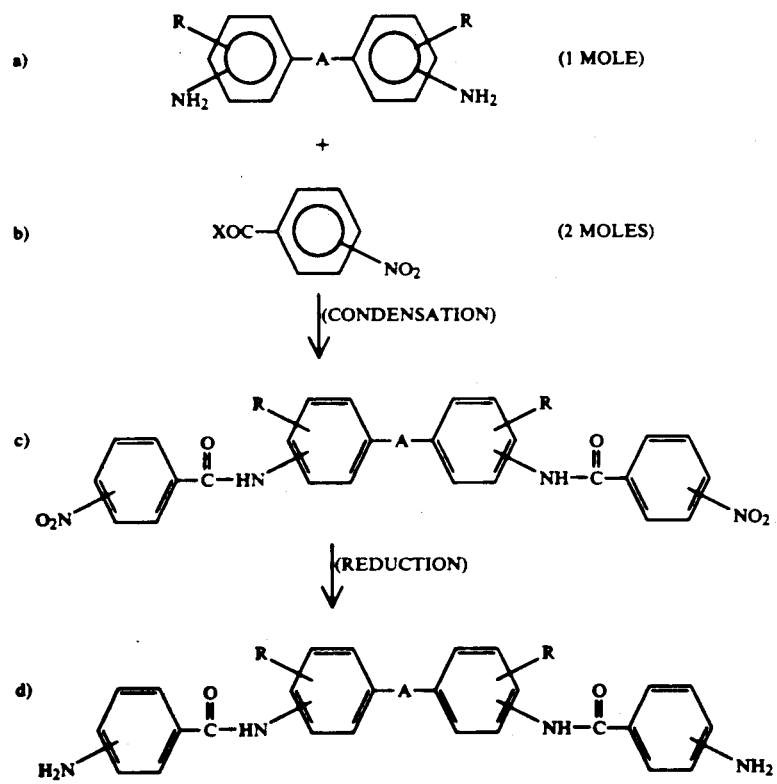

wherein R, A and X have the meanings set forth above.

To effect the initial reaction to prepare intermediate compounds of this invention of formula (c) above, a nitrobenzoyl halide of formula (b) is condensed with a diamine of formula (a). Preferably, the reaction is conducted using a low temperature solution condensation process at temperatures within the range of from about 25° to about 75° C., and under conditions which favor the reaction of the benzoyl halide substituent with the able solvent, such as ethyl acetate, in a Parr bottle, pressurizing the system with hydrogen gas and shaking the bottle vigorously at moderate temperatures of from about 50° to 55° C. in an appropriate apparatus until reduction is complete. The final reaction product may be then recovered by evaporating off the solvent or by precipitation techniques.

The following examples are illustrative of the invention.

EXAMPLE 1

Bis-N,N'-(para-nitrobenzoyl)-hexafluoro-2,2-bis(4-hydroxyphenyl)propane having the following structure is prepared:

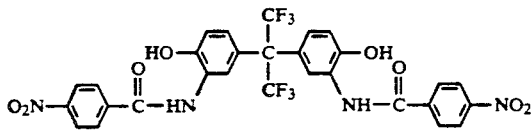

A 500 ml. round bottom flask equipped with a cooling jacket and mechanical stirrer was charged with 30.0 grams (0.082 mole) of 2,2-bis(3-amino-4-hydroxyphenyl) hexafluoropropane and 400 mls. of acetone. The mixture was stirred until the aminophenol had dissolved, after which 39.6 grams (0.213 mole) of para-nitrobenzoyl chloride dissolved in 100 mls. of acetone was added dropwise over a period of 30 minutes. The mixture was maintained at less than 20° C. during the addition, after which the mixture was heated with agitation at 35°-40° C. for a period of two hours. 30.0 grams (0.218 mole) of potassium carbonate was then added gradually and the mixture was agitated for two additional hours at 35°-40° C. The heat was removed and the mixture was agitated for an additional 18 hours at room temperature. Thereafter, 20 mls. of water and 16 mls. of a 50% solution of sodium hydroxide was added with vigorous agitation and the mixture was heated at 50°-55° C. for 30 minutes. The heat was then removed and the mixture was transferred to a beaker and the pH was adjusted in the range of 6.0 to 7.0 by addition of HCL (37%) and 500 ml of additional water, added incrementally over a period of 30 minutes under agitation. The mixture was then filtered on a 11 cm. Buchner filter, and the precipitate was washed with water and dried in an oven at 60°-70° C. The yield of bis-N,N'-(para-nitrobenzoyl)-hexafluoro-2,2-bis(4-hydroxyphenyl)propane was 93.6% of theoretical.

EXAMPLE 2

The product of Example 1 was purified by recrystallization in accordance with the following method.

A 1000 ml. round bottom flask equipped with a mechanical stirrer was charged with 51.0 grams of the crude product of Example 1, 316 grams of acetone and 158 grams of methanol.

The mixture was stirred and heated at 40°-50° C. until the product of Example 1 had dissolved. The mixture was cooled to room temperature and 30 grams of Norite (activated charcoal) was gradually added after which the mixture was stirred for about 25 minutes. The mixture was then clarified by passing it through a 9 cm. Buchner funnel and using a small amount of a 2 to 1 mixture of acetone/methanol as a rinse. The clarified solution was then transferred to a beaker and heated to 50°-55° C. 300 mls. of warm tap water was added dropwise to the solution over a period of 30 minutes, after which the solution was heated to 60°-65° C. After removal from the heat, the solution was allowed to cool slowly to 20°-25° C. which caused a precipitate of the purified compound to be formed. The mixture was filtered using a 9 cm. Buchner funnel, washed with tap water, and oven dried at 60°-70° C. The yield of product was 44 grams which represents an 86.2% recovery.

EXAMPLE 3

This example illustrates the preparation of bis-N,N'-(para-aminobenzoyl)-hexafluoro-2,2-bis(4-hydroxyphenyl propane by a reduction of the purified product of Example 2. The product prepared according to this Example has the structure:

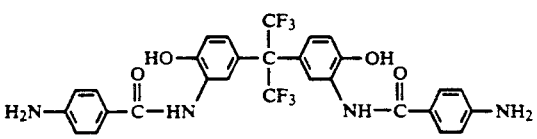

A one liter Parr bottle was charged with 20.0 grams (0.03 mole) of the purified product of Example 2, 1.0 grams of a 5% palladium on carbon catalyst and 180.4 grams of ethyl acetate to form a slurry. The slurry was purged by bubbling nitrogen gas through it for 15 minutes. The bottle was then connected to a shaker apparatus capable of maintaining intimate contact between gas, liquid, and solid phases, following which the slurry was purged three times with hydrogen gas to insure a pressure tight seal. The shaker was started and the contents were subjected to 50 psi hydrogen gas while heating at 50°-55° C. After the uptake stopped, the mixture was shaken for about 35 minutes. The mixture was then cooled to 35° C. After purging the resulting slurry with nitrogen, it was filtered to remove the catalyst, after which the solvent was evaporated. The product was heated in an air oven at 90° C. until dry, yielding 17.0 grams of dried product.

Other dinitro and diamino compounds within the scope of the present invention may be prepared by the processes described above or variations thereof which will be evident to those skilled in the art.

As set forth above, one of the uses of the diamino monomers of the present invention of formula I above where R' is NH$_2$ is in the synthesis of polyamide, polyimide and polyamide-imide polymers by reaction with aromatic dianhydrides, aromatic diacid halides or mixtures of these. In addition, the diamino monomers of formula I above wherein R' is NH$_2$ and R is OH or alkoxy may be used to prepare the corresponding polybenzoxazole-polyamides and polybenzoxazole-polyamide-polyimides. These polymers are useful in high temperature applications requiring good film-forming properties, molding properties and flexibility as well as excellent dielectric properties, such as dielectric insulating layers, fibers, composites, molded aerospace parts, photoresist layers, photoresist components and the like.

The following example illustrates the preparation of a polybenzoxazole-polyimide polymer.

EXAMPLE 4

In a three neck 100 ml flask equipped with a thermometer, condenser, dean stark trap mechanical stirrer and nitrogen inlet tube, 3.02 grams (0.005 moles) of the diamine produced in Example 3 and 2.22 grams (0.005 moles) of 2,2-bis-(3,4-dicarboxyphenyl) hexafluoropropane dianhydride were added to the flask along with 32 ml. of monochlorobenzene and 8 ml. of N-methyl pyrrolidone (NMP). The contents of the flask were heated to 90° C. under agitation after which 0.06 grams of para-toluene sulfonic acid was added. The mixture was heated to reflux temperature at 142° C. after which an additional 16 ml of monochlorobenzene and 4 ml of NMP were added. The contents of the flask were refluxed at 142°-145° C. for 10 hours. 20 ml of NMP was then added and the monochlorobenzene was distilled off at 155° C. The reaction mixture was then cooled to room temperature and precipitated using an ice/water/-methanol mixture. The precipitate was washed with water and oven dried overnight at 125° C.

The resulting polymer has an inherent viscosity of 0.60 dl/g in dimethylacetamide as a 0.5% by weight solution at 25° C. and a number average molecular weight of 37,000.

The polymer was dissolved in NMP to form a solution which was cast on a glass plate. The coated plate was subjected to an oven heating cycle to cyclize the polyamic acid portion of the linkage to form a polyamide-imide polymer, e.g., 70° C./1 hour, 100° C./1 hour, 150° C./1 hour, and 250° C./1 hour. A uniform flexible polymer film was obtained having a glass transition temperature of 345° C., and which remained soluble in NMP. The film was then further heated for 2 hours at 350° C. to obtain a polybenzoxazole-polyimide film having a glass transition temperature of 367° C., which was insoluble in NMP.

The use of the novel diamine monomers of the present invention in the preparation of polyamide-polyimide, polyamide-polyamide, polyamide-amide-polyimide, and the polybenzoxazole counterpart polymers is disclosed and claimed in copending applications Ser. Nos. 07/321,021, 07/321,039 and 07/321,024 filed in the United States Patent and Trademark Office on even date herewith, the disclosure of which applications is incorporated herein by reference.

It is to be understood that the above described embodiments of the invention are illustrative only and that modifications throughout may occur to those skilled in the art. Accordingly, this invention is not to be regarded as limited to the embodiments disclosed herein, but is to be limited as defined by the appended claims.

What is claimed is:

1. A compound of the formula:

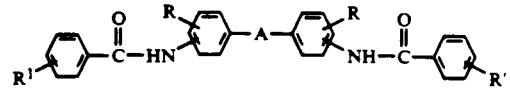

wherein A is perfluoroalkyl having from 1 to 10 carbon atoms; R is selected from the group consisting of hydroxy and $C_1$ to $C_4$ alkoxy; and R' is selected from the group consisting of $NO_2$ and $NH_2$.

2. The compound of claim 1, wherein A is

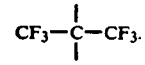

3. The compound of claim 2, wherein R is hydroxy.
4. The compound of claim 2, wherein R' is $NO_2$.
5. The compound of claim 2, wherein R' is $NH_2$.
6. A compound of the formula:

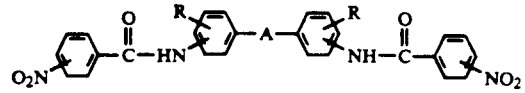

wherein A is perfluoroalkyl having from 1 to 10 carbon atoms; and R is selected from the group consisting of hydrogen, hydroxy and $C_1$ to $C_4$ alkoxy.

7. The compound of claim 6, wherein A is

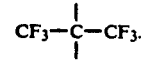

8. The compound of claim 7, wherein R is hydroxy.
9. The compound of claim 8, wherein R is para and the amino linkage is meta with respect to the A group.
10. The compounds of claims 7 or 8, wherein $NO_2$ is para with respect to the amido linkage.
11. The compound of claim 6, wherein R is para and the amido linkage is meta with respect to the A group, and $NO_2$ is para with respect to the amido linkage.

* * * * *